(12) United States Patent
Nakao

(10) Patent No.: US 6,743,425 B2
(45) Date of Patent: Jun. 1, 2004

(54) THERAPEUTIC AGENTS FOR ACHONDROPLASIA

(75) Inventor: Kazuwa Nakao, 4-1-2, Ooekitakutsukake-cho, Nishikyo-ku, Kyoto-shi, Kyoto (JP)

(73) Assignee: Kazuwa Nakao, Kyoto (JP)

(*) Notice: Subject to any disclaimer, the term of this patent is extended or adjusted under 35 U.S.C. 154(b) by 78 days.

(21) Appl. No.: 10/218,109

(22) Filed: Aug. 14, 2002

(65) Prior Publication Data

US 2003/0068313 A1 Apr. 10, 2003

(30) Foreign Application Priority Data

Sep. 28, 2001 (JP) ..................................... 2001-301586
Oct. 5, 2001 (JP) ..................................... 2001-310322

(51) Int. Cl.$^7$ ..................... A61K 38/47; C12N 15/09; C07H 21/02; G01N 33/00; A01K 67/027
(52) U.S. Cl. ............................... 424/94.61; 435/320.1; 435/325; 514/12; 536/23.1; 800/3; 800/9; 800/14; 800/18
(58) Field of Search ................... 424/94.61; 435/320.1, 435/325; 514/12; 536/23.1; 800/3, 9, 14, 18

(56) References Cited

U.S. PATENT DOCUMENTS 6,369,295 B1 * 4/2002 Cheah et al. .................. 800/18

FOREIGN PATENT DOCUMENTS

| JP | 04-074198 | 3/1992 |
|---|---|---|
| JP | 04-120094 | 4/1992 |
| JP | 04-120095 | 4/1992 |
| JP | 04-139199 | 5/1992 |
| JP | 06-009688 | 1/1994 |
| WO | WO 91/16342 | 10/1991 |
| WO | WO 02/074234 A2 | 9/2002 |

OTHER PUBLICATIONS

Chinkers et al., "Signal transduction by guanylyl cyclases," Annu. Rev. Biochem. 60, pp. 553–575 (1991).
Chusho et al., "Dwarfism and early death in mice lacking C–type natriuretic peptide," Proc. Natl. Acad. Sci. U.S.A. 98, pp. 4016–4021 (2001).
Hagiwara et al., "Autocrine regulation of rat chondrocyte proliferation by natriuretic peptide C and its receptor, natriuretic peptide receptor–B," J. Biol. Chem. 269, pp. 10729–10733 (1994).
Inoue et al., "Reciprocal regulation by cyclic nucleotides of the differentiation of rat osteoblast–like cells and mineralization of nodules," Biochem. Biophys. Res. Commun. 215, pp. 1104–1110 (1995).
Kojima et al., "Cloning and sequence analysis of a cDNA encoding a precursor for rat C–type natriuretic peptide (CNP)," FEBS Lett. 276, pp. 209–213 (1990).
Koller et al., "Selective activation of the B natriuretic peptide receptor by C–type natriuretic peptide (CNP)," Science 252, pp. 120–123(1991).
Komatsu et al., "C–type natriuretic peptide (CNP) in rats and humans," Endocrinology 129, pp. 1104–1106 (1991).
Komatsu et al., "Regulation of endothlial production of C–type natriurectic peptide in coculture with vascular smooth muscle cells," Circ. Res. 78, pp. 606–614 (1996).
Mericq et al., "Regulation of fetal rat bone growth by C–type natriuretic peptide and cGMP," Pediatr. Res. 47, pp. 189–193 (2000).
Metsäranta et al., "Developmental expression of a type II collagen/β–galactosidase fusion gene in transgenic mice," Dev. Dyn. 204, pp. 202–210 (1995).
Minamino et al., "N–terminally extended form of C–type natriuretic peptide (CNP–53) identified in porcine brain," Biochem. Biophys. Res. Commun. 170, pp. 973–979 (1990).
Mukoyama et al., "Brain natriuretic peptide as a novel cardiac hormone in humans," J. Clin. Invest. 87, pp. 1402–1412 (1991).
Naski et al., "Repression of hedgehog signaling and BMP4 expression in growth plate cartilage by fibroblast growth factor receptor 3," Development 125, pp. 4977–4988 (1998).
Ogawa et al., "Molecular cloning of the complementary DNA and gene that encode mouse brain natriuretic peptide and generation of transgenic mice that overexpress the brain natriuretic peptide gene," J. Clin. Invest. 93, pp. 1911–1921 (1994).
Rosenzweig et al., "Atrial natriuretic factor and related peptide hormones," Annu. Rev. Biochem. 60, pp. 229–255 (1991).
Rousseau et al., "Mutations in the gene encoding fibroblast growth factor receptor–3 in achondroplasia," Nature 371, pp. 252–254 (1994).
Shiang et al., "Mutations in the transmembrane domain of FGFR3 cause the most common genetic form of dwarfism, achondroplasia," Cell 78, pp. 335–342 (1994).
Shukunami et al., "Cellualr hypertrophy and calcification of embryonal carcinoma–derived chondrogenic cell line ATDC5 in vitro," J. Bone. Miner. Res. 12, pp. 1174–1188 (1997).
Stamoyannou et al., "Growth and growth hormone therapy in children with achondroplasia: a two–year experience," American Journal Of Medical Genetics 72, pp. 71–76 (1997).

(List continued on next page.)

Primary Examiner—Jon P. Weber
Assistant Examiner—Kailash C. Srivastava
(74) Attorney, Agent, or Firm—Hunton & Williams LLP

(57) ABSTRACT

The present invention aims to provide novel therapeutic agents for achondroplasia caused by mutations in FGFR3.

Therapeutic agents for achondroplasia caused by the cartilage growth inhibition resulting from mutations in the gene for fibroblast growth factor receptor 3 (FGFR3), comprising a substance activating guanylyl cyclase B (GC-B) as an active ingredient are disclosed.

5 Claims, 7 Drawing Sheets

OTHER PUBLICATIONS

Suda et al., "C–type natriuretic peptide as an autocrine/paracrine regular of osteoblast," Biochem. Biophys. Res. Commun. 223, pp. 1–6 (1996).

Suda, "Skeletal overgrowth in transgenic mice that overexpress brain natriuretic peptide," Proc. Natl. Acad. Sci. U.S.A. 95, pp. 2337–2342 (1998).

Sudoh et al., "A C–type natriuretic peptide (NP): new member of natriuretic peptide family identified porcine brain," Biochem., Biophys. Res. Commun. 168, pp. 863–870 (1990).

Tanaka et al., "Effect of growth hormone therapy in children with achondroplasia: growth pattern, hypothalamic–pituitary function, and genotype," European Journal of Endocrinology 138, pp. 275–280 (1998).

Yasoda et al., "Natriuretic peptide regulation of endochondral ossification," J. Biol. Chem. 273, pp. 11695–11700 (1998).

Yasoda et al., Abstract for the 72th Congress of the Japan Endocrine Society 74, p. 87 (1999).

* cited by examiner

A

B

C

THERAPEUTIC AGENTS FOR ACHONDROPLASIA

BACKGROUND OF THE INVENTION (i) Field of the Invention

The present invention relates to agents and methods for treating achondroplasia.

(ii) Description of the Related Art

Achondroplasia is one of the most common congenital diseases responsible for micromelic dwarfism characterized by short limbs relative to trunk. It is diagnosed by X-ray photographs in addition to growth failure in the major axes of the long bones of extremities and typical physical features such as a large frontally projecting cranium and a short nose. The disease is said to occur at an incidence of one to 10,000–25,000 people. This disease is an autosomal dominant hereditary disorder, but 80–90% of cases are found to be sporadic. Current therapies include orthopedic surgeries such as artificial hip joint replacement or leg lengthening and growth hormone therapy. Leg lengthening involves cutting bones at the age of 10 years or after and gradually increasing body height using a special device (leg lengthening device) over several courses of about six months. However, this procedure inflicts a great pain on patients. Growth hormone therapy increases body height by means of periodic growth hormone injections starting from childhood. However, growth ceases when injections are stopped. Neither therapy is curative, and neither are considered ideal from the viewpoint of patients' QOL (American Journal of Medical Genetics 72: 71–76, 1997; European Journal of Endocrinology 138: 275–280, 1998). Consequently, it is desirable to develop a achondroplasia therapy based on a new mechanism.

Recent reports show that achondroplastic patients have mutations in fibroblast growth factor receptor 3 (FGFR3) located at chromosome 4p16.3, and two mutations are currently known. Of these mutations, 97% represents G1138A (change of 1138th G to A) and 2.5% represents G1138C (change of 1138th G to C), resulting in a change of the amino acid Gly at the 380-position to Arg (G380R) (Nature 371: 252–254, 1994; Cell 78: 335–342, 1994). To examine the relation of this mutation to achondroplasia, G380R FGFR3 (sometimes hereinafter referred to as FGFR3$^{ach}$) transgenic mice were bred to provide an animal model for human achondroplasia. The mice showed short limbs and craniofacial hypoplasia (Development. 125: 4977–4988, 1998).

On the other hand, the natriuretic peptide (NP) family consists of three peptides, ANP (atrial natriuretic peptide), BNP (brain natriuretic peptide) and CNP (C-type natriuretic peptide), and is thought to show biological activity by increasing intracellular cGMP through two guanylyl cyclase coupled receptors (GC-A receptor for ANP and BNP, and GC-B receptor for CNP) (Annu. Rev. Biochem. 60: 229–255, 1991). NPs are reported to have important roles in the regulation of body fluid homeostasis and blood pressure control (J. Clin. Invest. 93: 1911–1921, 1987; J. Clin. Invest. 87: 1402–1412, 1994), but also they are known by their expression and physiological activity in various tissues other than cardiovascular system (Endocrinology. 129: 1104–1106, 1991; Annu. Rev. Biochem. 60: 553–575, 1991). Among them, they have a role as bone growth factor. In organ cultures of tibiae from fetal mice, CNP significantly promotes longitudinal bone growth (J. Biol. Chem. 273: 11695–11700, 1998). CNP is more potent than ANP and BNP in the production of cGMP in organ cultures of tibiae from fetal mice, cultured chondrocytes and cultured osteoblasts (J. Biol. Chem. 269: 10729–10733, 1994; Biochem. Biophys. Res. Commun. 223: 1–6, 1996; Biochem. Biophys. Res. Commun. 215: 1104–1110, 1995). CNP and its receptor GC-B are expressed in the growth plates of bones (J. Biol. Chem. 273: 11695–11700, 1998; Proc. Natl. Acad. Sci. U.S.A. 95: 2337–2342, 1998). CNP was also found to have a role in thickening the cartilage layer of the growth plate in transgenic mice expressing CNP specifically in cartilage (Yasoda et al., Abstracts of the 72nd meeting of the Japan Endocrinology Society, 1999).

The relation of CNP to dwarfism was also indicated because CNP knockout mice developed dwarfism (Proc. Natl. Acad. Sci. U.S.A. 98: 4016–4021, 2001), but nothing has been described about its relation to achondroplasia caused by FGFR3 mutations and no positive evidence has shown that CNP is effective for achondroplasia caused by FGFR3 mutations. That is, it is known that FGFR3 mutations are related with achondroplasia and that CNP is involved in chondrogenesis, but nothing has been known so far about the relation between them, particularly which of FGFR3 and CNP is located upstream in the regulatory pathway of endochondral ossification and whether or not CNP has a therapeutic effect for achondroplasia.

An object of the present invention is to provide novel agents and methods for treating achondroplasia caused by mutations in FGFR3.

SUMMARY OF THE INVENTION

On the hypothesis that a substance (e.g., CNP) activating guanylyl cyclase B (GC-B) may be applied to diseases involving chondrogenesis, we searched for a suitable achondroplasia model and mated this animal model with CNP-transgenic mice to prepare double transgenic mice for testing whether the symptoms of achondroplasia can be corrected. As described above, G380R FGFR3 (FGFR3$^{ach}$) transgenic mice had been bred as an animal model of human achondroplasia, which showed short limbs and craniofacial hypoplasia (Development. 125: 4977–4988, 1998). Thus, we obtained such FGFR3$^{ach}$-transgenic mice and mated them with our CNP-transgenic mice to prepare CNP/FGFR3$^{ach}$-double transgenic mice, which were found to remedy the bone growth inhibition caused by FGFR3$^{ach}$, whereby we achieved the present invention relating to agents and methods for treating achondroplasia with CNP.

Accordingly, the present invention provides therapeutic agents for achondroplasia caused by the cartilage growth inhibition resulting from mutations in the gene for fibroblast growth factor receptor 3 (FGFR3), containing a substance activating guanylyl cyclase B (GC-B) as an active ingredient, as well as methods for treating achondroplasia comprising administering a substance activating guanylyl cyclase B (GC-B).

As used herein, the expression "achondroplasia caused by the cartilage growth inhibition resulting from mutations in the gene for fibroblast growth factor receptor 3 (FGFR3)" means achondroplasia caused by hyperactivity or function control failure of FGFR3 or overexpression of the FGFR3 gene resulting from mutations in the FGFR3 gene, and achondroplasia is synonymous with chondrogenesis disorder. As used herein, FGFR3$^{ach}$ means fibroblast growth factor receptor 3 (FGFR3) containing a mutation of the amino acid Gly at the 380-position substituted to Arg (G380R), which is known to induce hyperactivity of FGFR3 (Development. 125: 4977–4988, 1998).

As used herein, the expression "substance activating guanylyl cyclase B" means a substance (peptide or low molecular compound) capable of binding to GC-B known as a receptor for CNP (C-type natriuretic peptide) to activate it, preferably a substance (peptide or low molecular compound) having CNP (C-type natriuretic peptide)-like activity, such as mammalian CNP (CNP-22 (Biochem. Biophys. Res. Commun. 168: 863–870, 1990, WO91/16342), CNP-53 (Biochem. Biophys. Res. Commun. 170: 973–979, 1990, JPA 1992-74198, JPA 1992-139199), avian CNP (JPA 1992-120094), amphibian CNP (JPA 1992-120095) and CNP analog peptides (JPA 1994-9688), preferably mammalian CNP, more preferably CNP-22. Identification of the "substance activating guanylyl cyclase B" is performed by, for example, expressing GC-B receptor in cultured cells such as COS-7, incubating the medium with a candidate substance (peptide or low molecular compound) at a given temperature for a given period (e.g., 37° C., 5 min) and then determining the concentration of cGMP in the cell extracts (Science 252: 120–123, 1991).

DETAILED DESCRIPTION OF PREFERRED EMBODIMENTS OF THE INVENTION

Figure 1:
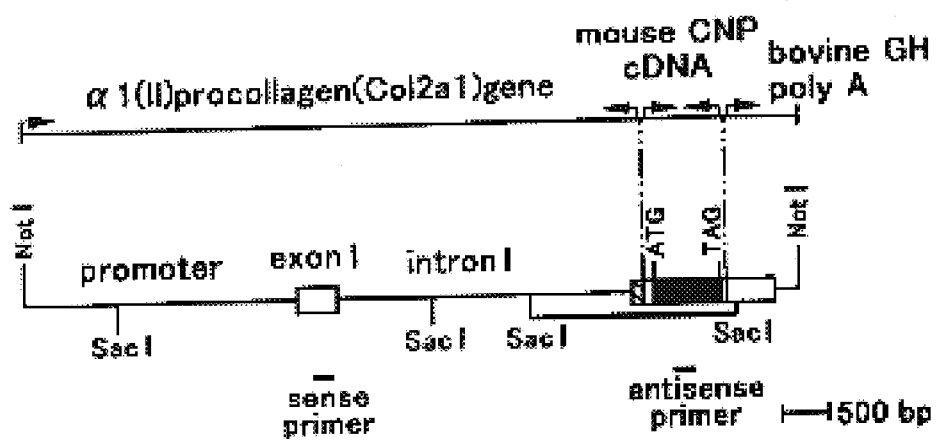
FIG. 1 shows generation of transgenic mice that overexpress CNP specifically in cartilage. A: Schematic representation showing the structure of a recombinant gene for generating CNP-transgenic mice. B: Photograph showing the results of Southern hybridization using the tail DNA of CNP-transgenic mice. C: Photographs showing the results of RT-PCR analysis of the expression of Col II-CNP in various organs from CNP-transgenic mice.
Figure 1:
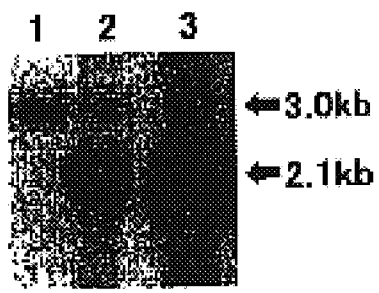
Figure 1:
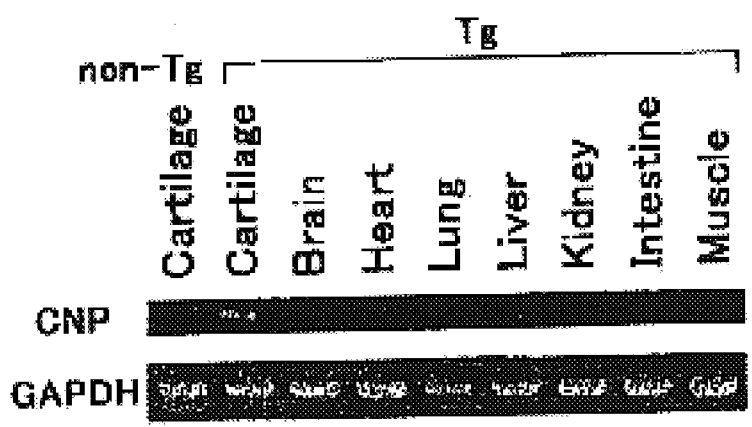

The CNP-transgenic mice prepared by us increased their body length with longitudinal overgrowth of bones through endochondral ossification. Further analysis of the CNP-transgenic mice by histochemical analysis of the growth plate showed 1) increased thickness of the growth plate along with the elongation of both proliferative and hypertrophic chondrocyte layers, 2) enlarged extracellular matrix in the proliferative chondrocyte layer, and 3) increased size of the mature hypertrophic chondrocytes. These facts show that CNP promotes the expression of the differentiation trait of chondrocytes in each differentiation stage of the growth plate, rather than contributes to the commitment to the differentiation or proliferation of chondrocytes of the growth plate, along with the fact that no appreciable alteration in the proliferation of chondrocytes was observed as assayed by BrdUrd staining in the hypertrophic chondrocyte layers of the growth plate of the CNP-transgenic mice. This is supported by the fact that the expression of type X collagen mRNA in the hypertrophic chondrocytes in the growth plate of the CNP-transgenic mice had an intensity comparable to that of their nontransgenic littermates though the expression cell area enlarged. However, the width of the cranium, which is made through membranous ossification, was not changed in the CNP-transgenic mice. This suggests that CNP is not expressed in the cranium, or is not involved in the process of membranous ossification.

Ex vivo organ culture experiments provided further information about the action mechanism of CNP in the growth plate. The elongation of the cartilagenous primordia with enlarged extracellular matrix and increased size of hypertrophic chondrocytes in cultured tibiae from CNP-transgenic mice was potent, as obtained in cultured tibiae from their nontransgenic littermates in the presence of $10^{-7}$ M CNP. This histological change was completely abolished by adding a non-peptide NP receptor antagonist HS-142-1 (Circ. Res. 78: 606–614, 1996), like the case when HS-142-1 was added to cultured tibiae from their nontransgenic littermates incubated with $10^{-7}$ M CNP. These results show that the Col II-CNP transgene (the gene containing a mouse CNP cDNA fragment inserted into a DNA segment of the mouse procollagen al type II (Col 2a1) promoter region as described in Example 1) functions well to alter the phenotype in vivo in the growth plate cartilage, along with the fact that the production of the second messenger of CNP, cGMP, increases in cultured tibiae from CNP-transgenic mice. The increase in the synthesis of the extracellular matrix, as shown by the increase of $^{35}$S incorporation in cultured tibiae from CNP-transgenic mice, is compatible with the enlargement of the extracellular matrix in the growth plate of CNP-transgenic mice. This can explain the elongation mechanism of the growth plate in CNP-transgenic mice. The elongation of metaphyseal cancellous bone observed in CNP-transgenic mice indicates that the replacement of cartilage to calcified bone was proceeded smoothly. These experiments revealed the importance of CNP in endochondral ossification.

Next, we obtained G380R FGFR3 (FGFR3$^{ach}$)-transgenic mice (from Professor David M. Ornitz of Washington University, US) and mated them with CNP-transgenic mice to prepare CNP/FGFR3$^{ach}$-double transgenic mice. In CNP/FGFR3$^{ach}$-double transgenic mice, both CNP-Tg gene and FGFR3$^{ach}$-Tg gene are expressed in the resting chondrocyte layer and proliferative chondrocyte layer of the growth plate and the symptoms of dwarfism of FGFR3$^{ach}$-transgenic mice were visibly improved. The endogenous CNP, GC-B and FGFR3 were expressed in the proliferative chondrocyte layer and the prehypertrophic chondrocyte layer.

Figure 6:
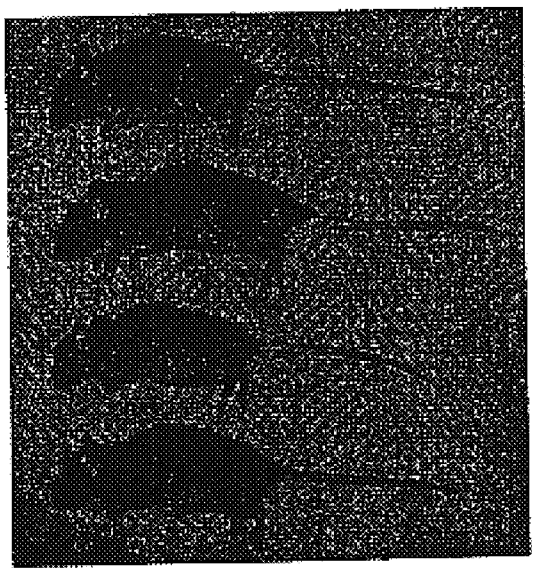
FIG. 6 shows gross phenotypes of CNP-transgenic, FGFR3$^{ach}$-transgenic and CNP/FGFR3$^{ach}$-double transgenic mice. A: Photographs showing the gross appearance of 3-mo-old nontransgenic littermate, CNP-transgenic mice, FGFR3$^{ach}$-transgenic mice and CNP/FGFR3$^{ach}$-double transgenic mice from top to bottom. B: Graph showing the growth curves of the naso-anal length of female FGFR3$^{ach}$-transgenic mice (closed triangles), female CNP/FGFR3$^{ach}$-transgenic mice (open squares) and nontransgenic littermates (closed circles) (n=7). C: Photographs showing detection of the expression of Col II-CNP by RT-PCR using total RNA from the cartilage of nontransgenic littermates (lane 1), CNP-transgenic mice (lane 2) and FGFR3$^{ach}$-transgenic mice (lane 3). D: Left panel shows photographs showing the appearance of the skeleton of 3-mo-old nontransgenic littermates, CNP-transgenic mice, FGFR3$^{ach}$-transgenic mice and CNP/FGFR3$^{ach}$-double transgenic mice from top to bottom. Right panel shows a graph showing comparison of the length of various bones of nontransgenic littermates (open bar), CNP-transgenic mice (closed bar), FGFR3$^{ach}$-transgenic mice (hatched bar) and CNP/FGFR3$^{ach}$-double transgenic mice (shaded bar) (n=4). *$P<0.05$. The lengths of cranium (naso-occipital), cranium (width), humerus, femur and vertebra are shown.
Figure 6:
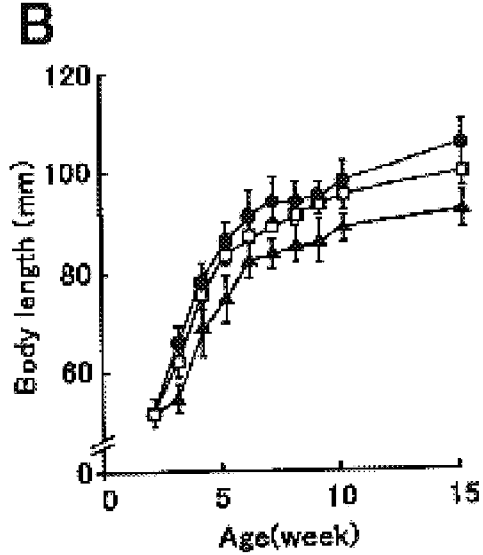
Figure 6:
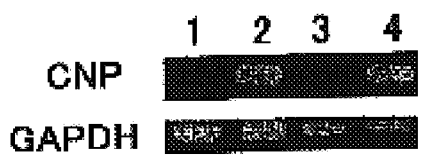
Figure 6:
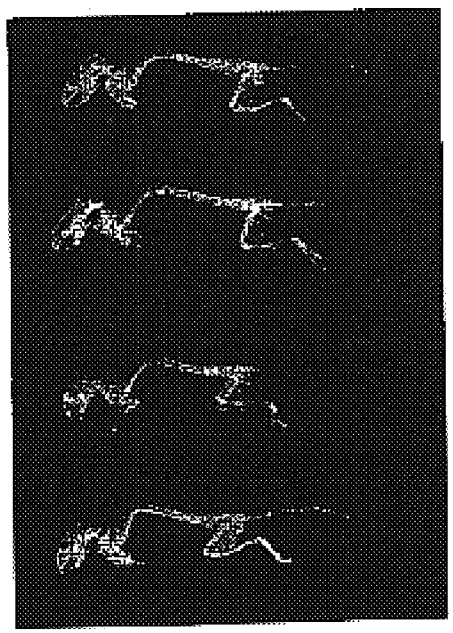
Figure 6:
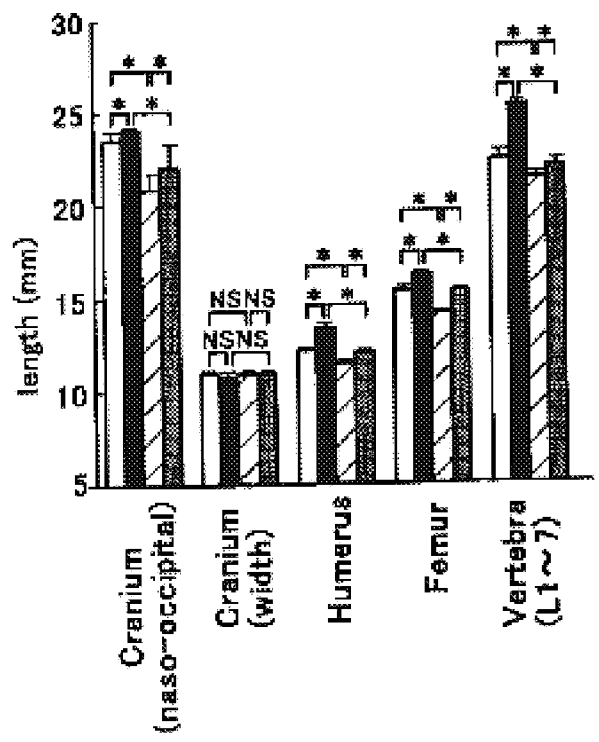

The effect of the present invention is best shown in FIG. 6. FIG. 6A shows the gross appearance of 3-mo-old nontransgenic littermates, CNP-transgenic mice, FGFR3$^{ach}$- transgenic mice and CNP/FGFR3$^{ach}$-double transgenic mice from top to bottom, and FIG. 6D shows their skeletal appearance. The naso-anal length of CNP/FGFR3$^{ach}$-double transgenic mice is almost comparable to that of nontransgenic littermates, showing that the shortening of the length of the limbes observed in FGFR3$^{ach}$-transgenic mice can be rescued by the overexpression of CNP.

The fact that CNP improved the symptoms of dwarfism of FGFR3$^{ach}$-transgenic mice suggests that CNP is not, at least in most part, located upstream of FGFR3 in the regulatory pathway of endochondral ossification. The shortened growth plate in FGFR3$^{ach}$-transgenic mice was elongated by the overexpression of CNP in both proliferative and hypertrophic chondrocyte layers, but some histological features were different from those of the nontransgenic littermates. The extracellular matrices of both proliferative and hypertrophic chondrocyte layers enlarged so that the alignment of hypertrophic chondrocytes was disordered or hypertrophic chondrocytes enlarged. Considering that overexpressed CNP did not affect the delayed formation of the secondary ossification center in FGFR3$^{ach}$-transgenic mice, CNP does not seem to be involved in the commitment to the differentiation of chondrocytes as FRFR3 does, but rather seems to promote the gene expression of chondrocytes in each differentiation stage. That is, the pathway in which CNP regulates endochondral ossification may be different from that of FGFR3.

Further in vitro study of the interaction between CNP and FGFR3 using a mouse chondrocyte strain showed that CNP/GC-B systems and basic FGF/FGFR3 systems (basic FGF is a ligand for FGFR3) together influence intracellular transmission of information in chondrocytes.

Without being bound to the specific theory described above, we confirmed from the results described above that the growth retardation of FGFR3$^{ach}$-transgenic mice is rescued by the overexpression of CNP though CNP and FGFR3 have different regulatory mechanisms of endochondral ossification. This suggested that CNP has a therapeutic effect as a drug for promoting the growth of long bones with the purpose of treating achondroplastic patients, whereby the present invention was achieved. A major known cause of achondroplasia is hyperactivity of FGFR3 resulting from mutations in the FGFR3 gene, but achondroplasic symptoms may also be caused by function control failure of FGFR3 and enhanced expression of the FGFR3 gene. A novel therapy can be provided for these achondroplasic symptoms by activating GC-B or promoting the gene expression, protein expression and protein function of its ligand CNP. To promote the gene expression of CNP, the expression of the endogenous CNP gene may be enhanced or gene therapy may also be applied by transferring an exogenous CNP gene into the living body.

Therapeutic agents for achondroplasia of the present invention are prepared from a substance activating GC-B as an active ingredient in combination with a carrier or exipient and other additives used for ordinary formulation.

Suitable carriers and excipients for formulation include, for example, lactose, magnesium stearate, starch, talc, gelatin, agar, pectin, acacia, olive oil, sesame oil, cacao butter, ethylene glycol and other common additives.

Suitable solid compositions for oral administration include tablets, pills, capsules, powders and granules. In such solid compositions, at least one active ingredient is mixed with at least one inert diluent, such as lactose, mannitol, glucose, hydroxypropylcellulose, microcrystalline cellulose, starch, polyvinylpyrrolidone, or magnesium aluminometasilicate. The compositions may conventionally contain additives other than inert diluents, e.g., lubricants such as magnesium stearate, disintegrants such as calcium carboxymethylcellulose, and solubilizers such as glutamic acid or aspartic acid. Tablets or pills may, if desired, be coated with a sugar coating or a gastric or enteric film comprising sucrose, gelatin, hydroxypropyl methylcellulose phthalate or the like or may be coated with two or more layers. Capsules of an absorbable material such as gelatin are also included.

Liquid compositions for oral administration include pharmaceutically acceptable emulsions, solutions, suspensions, syrups and elixirs, and may contain ordinary inert diluents, such as purified water and ethanol. In addition to inert diluents, these compositions may contain adjuvants such as wetting agents or suspending agents, sweetening agents, flavoring agents, aromatics and preservatives.

Injections for parenteral administration include sterile aqueous or nonaqueous solutions, suspensions and emulsions. Aqueous solutions and suspensions contain water for injection and physiological saline for injection, for example. Nonaqueous solutions and suspensions contain propylene glycol, polyethylene glycol, vegetable oils such as olive oil, alcohols such as ethanol, and POLYSORBATE 80 (registered trademark). These compositions may further contain adjuvants, such as preservatives, wetting agents, emulsifying agents, dispersing agents, stabilizers (e.g., lactose), and solubilizers (e.g., glutamic acid and aspartic acid). These can be sterilized by ordinary sterilizing methods, such as mechanical sterilization with a microfiltration membrane, heat sterilization such as autoclaving or inclusion of a bactericide. Injections may be solution formulations or freeze-dried formulations to be reconstituted before use. Suitable excipients for freeze-drying include, for example, sugar alcohols and sugars such as mannitol or glucose.

When therapeutic agents of the present invention are used for gene therapy, they may contain a substance activating GC-B such as a CNP-related nucleic acid integrated downstream of a promoter sequence that is functional in host cells such as Cytomegalovirus promoter (CMV promoter) in a virus vector, preferably a lentivirus vector, an adeno-associated virus vector, more preferably an adenovirus vector, or in a known vehicle suitable for gene therapy such as a chemically synthesized liposome, a virus envelope or a complex of a virus envelop and a chemical liposome.

Therapeutic agents for achondroplasia of the present invention are preferably administered via pharmaceutically common routes such as oral or parenteral routes. When the active ingredient is a GC-B agonist antibody, they are normally administered via parenteral routes such as injection (subcutaneous, intravenous, intramuscular or intraperitonial injection) or percutaneous, mucosal, nasal or pulmonary administration, but may also be orally administered.

The amount of the substance activating GC-B contained as an active ingredient in formulations of the present invention can be determined depending on the type of disease to be treated, the severity of the disease, the age of the patient and other factors, but generally can be administered in the range of 0.005 µg/kg-100 mg/kg, preferably 0.025 µg/kg-5 mg/kg.

Therapeutic agents for achondroplasia of the present invention can be used in combination with conventional therapies such as growth hormones or orthopedic surgeries such as artificial hip joint replacement or leg lengthening.

The present invention includes, but is not limited to, the following aspects.

(1) A therapeutic agent for achondroplasia caused by the cartilage growth inhibition resulting from mutations in the gene for fibroblast growth factor receptor 3 (FGFR3), containing a substance activating guanylyl cyclase B (GC-B) as an active ingredient.

(2) The agent as defined in (1) above wherein the cartilage growth inhibition is rescued by enlarging hypertrophic chondrocytes and increasing the extracellular matrix of the proliferative chondrocyte layer.

(3) The agent as defined in (1) or (2) above wherein the substance activating GC-B is a peptide.

(4) The agent as defined in (3) above wherein the peptide is a C-type natriuretic peptide (CNP).

(5) The agent as defined in (4) above wherein the CNP is CNP-22 or CNP-53.

(6) The agent as defined in (1) or (2) above wherein the substance activating GC-B is a low molecular compound.

(7) The agent as defined in (1) or (2) above wherein the agent containing a substance activating GC-B as an active ingredient promotes the gene expression, protein expression or protein function of the substance activating GC-B.

(8) The agent as defined in (1) or (2) above wherein the agent containing a substance activating GC-B as an active ingredient promotes the expression of a gene for CNP, the expression of a CNP protein or the function of a CNP protein.

(9) A method for treating achondroplasia caused by the cartilage growth inhibition resulting from mutations in the gene for fibroblast growth factor receptor 3 (FGFR3), comprising administering a substance activating guanylyl cyclase B (GC-B).

(10) The method as defined in (9) above, comprising rescuing the cartilage growth inhibition by enlarging hypertrophic chondrocytes and increasing the extracellular matrix of the proliferative chondrocyte layer.

(11) The method as defined in (9) or (10) above wherein the substance activating GC-B is a peptide.

(12) The method as defined in (11) above wherein the peptide is a C-type natriuretic peptide (CNP).

(13) The method as defined in (12) above wherein the CNP is CNP-22 or CNP-53.

(14) The method as defined in (9) or (10) above wherein the substance activating GC-B is a gene (for example, DNA) encoding a peptide.

(15) The method as defined in (14) above wherein the peptide is a C-type natriuretic peptide (CNP).

(16) The method as defined in (15) above wherein the CNP is CNP-22 or CNP-53.

(17) The method as defined in any one of (14) to (16) above, comprising transferring a gene encoding a peptide directly or in a vector (for example, adenovirus-derived vector) or a liposome suitable for gene therapy.

(18) A use of the substance as defined in any one of (3) to (6) above for preparing a therapeutic agent for achondroplasia caused by the cartilage growth inhibition resulting from mutations in the gene for fibroblast growth factor receptor 3 (FGFR3)

The following examples further illustrate the present invention.

EXAMPLES

Example 1

Preparation of a Recombinant Gene for Generating CNP-Transgenic Mice

As shown in FIG. 1A, a mouse CNP cDNA fragment encoding amino acid residues 1–127 (489 bp; FEBS Lett.

276: 209–213, 1990) was inserted into a DNA segment of the mouse procollagen al type II (Col 2a1) promoter region (6.5 kb; Dev. Dyn. 204: 202–210, 1995). This promoter region DNA segment was supplied from B. de Crombrugghe, M. D. Anderson Cancer Center, Huston. This promoter region DNA segment containing a promoter, exon 1, intron 1 and an artificial splice acceptor site was fused to the downstream CNP cDNA fragment. The initiation codon in exon 1 of this promoter region DNA segment was inactivated by point mutagenesis. A DNA segment (0.3 kb) containing a bovine growth hormone polyadenylation signal was added to the downstream of the CNP cDNA. The NotI/NotI DNA fragment (7.3 kb) as shown in FIG. 1A was purified for injection into fertilized oocytes and used as a col-CNP DNA solution.

Example 2

Generation of CNP-Transgenic Mice

The mice used for collecting fertilized eggs to be microinjected with the col-CNP DNA solution (hereinafter referred to as injecting DNA solution) were C57BL/6J inbred mice purchased from CLEA Japan, Inc. (egg collecting mice). Females at 8 weeks of age or older were superovulated and mated with males at 8 weeks of age or older to collect many fertilized eggs, which were transferred to M2 medium and cultured in a 5% carbon dioxide incubator at 37° C. Then, 2 pL of the injecting DNA solution was injected into the male pronucleus of each of said fertilized eggs by microinjection using a DNA injection pipette. The fertilized eggs injected with the injecting DNA solution were transferred to M16 medium and cultured overnight in a 5% carbon dioxide incubator at 37° C. The female mice used for pregnancy, delivery and nursing of offspring from the fertilized eggs injected with the injecting DNA solution (foster mother mice) and the male mice mated with the females were ICR inbred mice purchased from CLEA Japan, Inc. Vasoligated male mice at 8 weeks of age or older were mated with female mice at 8 weeks of age or older, among which those showing a vaginal plug were used as foster mothers. The left and right oviducts of each foster mother were exposed by surgery using an anesthetic intraperitoneally injected at 0.01 ml/g body weight containing Nembutal (Dainabot Co., Ltd., 50 mg/mL sodium pentobarbital) diluted to 12% in a diluent (a mixed solution of 20 mL propylene glycol, 10 mL ethanol and 70 mL sterilized water). Among the fertilized eggs cultured overnight, those having developed into 2-cell embryos were collected and 10–15 of them were inserted into each oviduct, after which the incised site was sutured. Foster mothers were raised for 3 weeks and if they delivered, the tail of each offspring was dissected at about 1 cm 5 weeks after birth to isolate and purify chromosomal DNA using Easy-DNA Kit (Invitrogen). This tail DNA was checked for the presence of the transgene by PCR. The mice in which the presence of the transgene was confirmed were reared as founder transgenic mice up to the age of 7 weeks and then naturally mated with nontransgenic C57BL/6J at 7 weeks of age or older to give transgenic progeny.

The gene microinjection experiment yielded 5278 eggs from a total of 336 egg-collecting mice C57BL/6J, and the injecting DNA solution was injected into 2280 eggs identified as fertilized eggs among them. On the following day, 1600 eggs (70%) developed into 2-cell embryos, 1476 of which were implanted into the oviducts of a total of 60 foster mothers. Thirty-seven foster mothers became pregnant and gave birth to a total of 108 offspring (7%). An assay for the transgene by PCR in the tail DNA showed that a total of 4 founder transgenic mice (4%) (2 males, 2 females) were obtained. These founder transgenic mice were naturally mated with nontransgenic C57BL/6J to give progeny in which the transgene was transmitted in two strains (male Tg-1055, female Tg-1077).

Example 3

Genetic Analysis of CNP-Transgenic Mice 3-1 Verification of Gene Transfer into Transgenic Mice by PCR The transgene was verified by Southern hybridization using the isolated and purified tail DNA. The tail DNA was digested with a restriction enzyme SacI and subjected to Southern hybridization with a $^{32}$P-labeled CNP cDNA fragment (526 bp) to give a 2.1 kb band for the transgene and a 3.0 kb band for the endogenous gene (FIG. 1B). The copy number was assessed by comparing the strength of the 2.1 kb band with the strength of the 3.0 kb endogenous band, and the male strain Tg-1055 shown to contain 10 copies was used for further analysis.

3-2 Expression Analysis of the IskD77N Gene by PCR

Expression analysis of the transgene was performed by the Real Time-PCR method. Cartilage from the lower vertebra and the tail and other organs were rapidly dissected from newborn nontransgenic and transgenic mice and stored in liquid nitrogen. They were homogenized by a Physcotoron homogenizer (NITION Medical Supply, Chiba, Japan) and then, total RNA was isolated and purified with an ISOGEN reagent. A Superscript first strand synthesis kit (GIBCO/BRL, Gaithersburg, Md.) was used to synthesize cDNA with oligo-dT primers, and PCR was then performed using the forward primer (in exon 1) and reverse primer (in cDNA) as shown in FIG. 1A. The PCR reaction involved 45 cycles of a three-step reaction consisting of 95° C. for 30 seconds, 58° C. for 30 seconds and 72° C. for 1 minutes. After the PCR reaction, a 10 µL aliquot was assayed by electrophoresis on 1% agarose gel. The 450-bp positive band was detected only in cartilage, but not in brain, heart, lung, liver, kidney, intestine and muscle. The 450-bp positive band was not detected in the cartilage and other organs of their nontransgenic littermates.

Example 4

Determination of the Growth Curve of CNP-Transgenic Mice

Figure 2:
FIG. 2 shows the appearance of CNP-transgenic mice. A: Photographs showing the skeletons of a nontransgenic mouse (upper) and a CNP-transgenic mouse (lower) at the age of 1 day. B: Graphs showing the growth curves of male (left) and female (right) CNP-transgenic mice including heterozygotes (closed circles) and homozycotes (closed squares) as compared with nontransgenic littermates (open circles). C: The left panel shows soft x-ray photographs of the cranium (upper) and the lower extremities (lower) of 6-mo-old female nontransgenic littermates (left) and female CNP-transgenic mice (right), and the right panel shows a graph showing comparison of the length of some bones of nontransgenic female littermates (open bar) and female CNP-transgenic mice (closed bar) measured from the photographs on the left panel.
Figure 2:
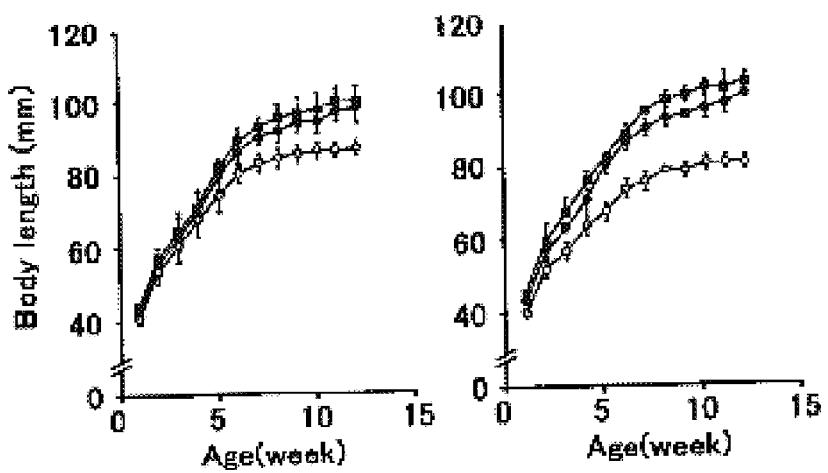
Figure 2:
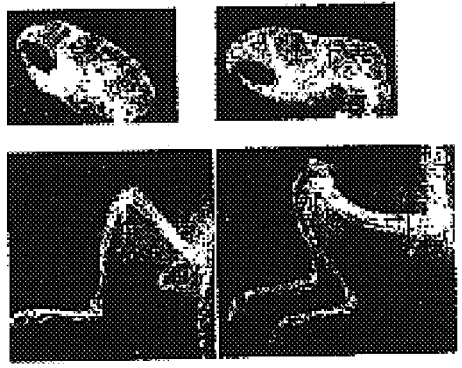
Figure 2:
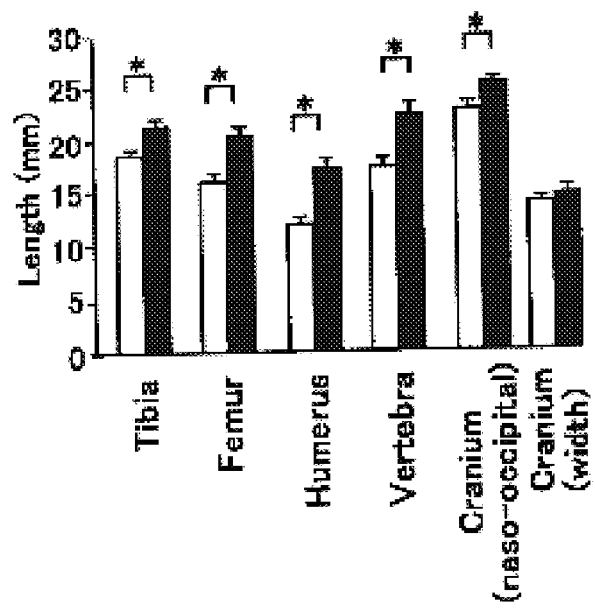

The length between the nose to the anus (hereinafter referred to as naso-anal length) was measured every week to draw a growth curve of mice. At the perinatal stage, CNP-transgenic mice and their nontransgenic littermates were not distinguished from each other. At 1 day after birth, Alzarin red S and Alcian blue staining of bones and cartilage revealed longitudinal overgrowth of both bones and cartilage in CNP-transgenic mice, including long bones of limbs, vertebrae and skulls (FIG. 2A). No delay in the ossification was observed in the periphery of limbs at this stage. Ossification centers of phalanges had already appeared in CNP-transgenic mice as well as their nontransgenic littermates. As they grew, CNP-transgenic mice gradually showed a prominent increase in the naso-anal length (FIG. 2B). Female 10-wk-old CNP-transgenic mice were 19% longer than their female nontransgenic littermates (n=7). Male CNP-transgenic mice were longer than their male nontransgenic littermates (n=7), but to an extent lower than female mice (10%). Homozygous CNP-transgenic male mice were longer than heterozygous CNP-transgenic male mice (female 6%, male 4%, n=7). Soft X-ray analysis showed a significant increase in 6-mo-old CNP-transgenic mice as compared with their nontransgenic littermates in the length of limbs, vertebrae and the longitudinal axis of the skull, all of which were formed by endochondral ossification, although the width of the cranium did not increase (FIG. 2C). The increase was especially prominent in vertebrae and proximal long bones (humerus and femur), which were longer by 28%, 25% and 23% (n=6) than those of their nontransgenic littermates, respectively.

Example 5

Histological Analysis of CNP-Transgenic Mice

For light microscopy, the tibiae and vertebrae were removed and fixed in 10% formalin/PBS (pH 7.4). The calcified bones were demineralized in 10% formalin/PBS (pH 7.4) containing 20% EDTA. Paraffin blocks were prepared by standard histological procedures. Sections (5–6 $\mu$m) were prepared at several levels and stained with Alcian blue (pH 2.5) and then counterstained with hematoxylin/eosin. The length of the layers of the growth plate, the diameter of the matured hypertrophic chondrocytes and the BrdUrd labeling index in the proliferative chondrocyte layer were analyzed on a Macintosh computer using an NIH Image program. For BrdUrd staining, 2-wk-old mice were intraperitoneally injected with BrdUrd (100 $\mu$g/g body weight) and killed after 1 h. Immunohistochemical staining of incorporated BrdUrd in cells in the growth plate of the tibiae was performed by standard methods. To evaluate the mineralized stage of each sample, Von Kossa staining was done on undecalcified sections.

For in situ hybridization analysis, digoxigenin-labeled sense and antisense riboprobes were prepared from a rat pro-a1(X) collagen cDNA fragment and a mouse pro-a1 (II) collagen cDNA fragment by using a digoxigenin RNA labeling kit (Roche Diagnostics, Indianapolis, Ind.).

Figure 3:
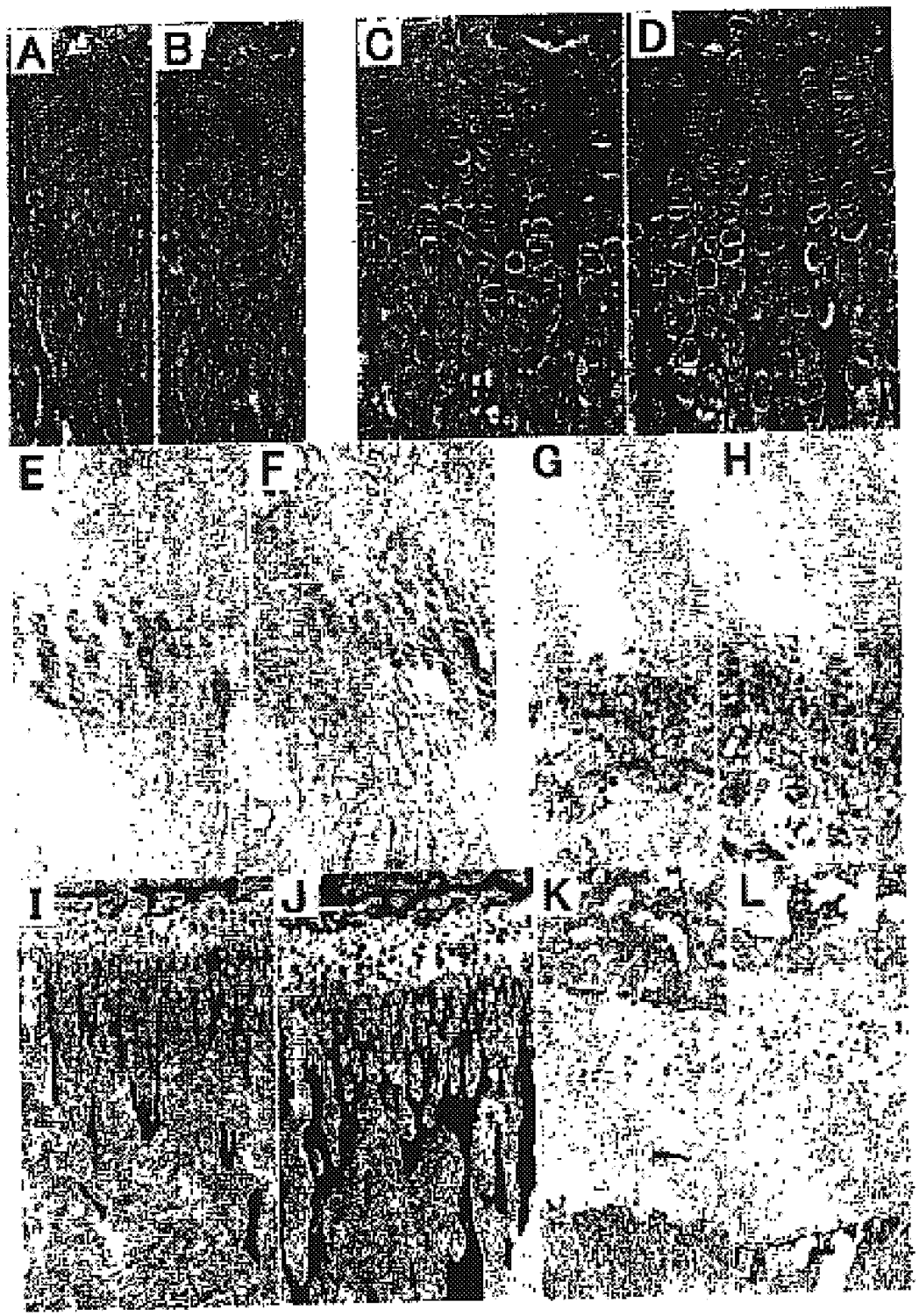
FIG. 3 shows histological analysis of the growth plate of CNP-transgenic mice. A–D: Photographs showing Alcian blue and hematoxylin/eosin staining (3-wk-old), A: tibial growth plate of nontransgenic littermates (x50), B: tibial growth plate of CNP-transgenic mice (x50), C: tibial growth plate of nontransgenic littermates (x200), D: tibial growth plate of CNP-transgenic mice (x200). E–H: Photographs showing in situ hybridization analysis with collagen cDNA probes (2-wk-old), E: tibial growth plate of nontransgenic littermates (type II collagen, x200), F: tibial growth plate of CNP-transgenic mice (type II collagen, x200), G: tibial growth plate of nontransgenic littermates (type X collagen, x200), H: tibial growth plate of CNP-transgenic mice (type X collagen, x200). I–J: Photographs showing von Kossa staining (3-wk-old), I: epiphyseal trabecular bones of nontransgenic littermates (x50), J: epiphyseal trabecular bones of CNP-transgenic mice (x50). X–L: Photographs showing Brdurd staining (2-wk-old), K: tibial growth plate of nontransgenic littermates (x50), L: tibial growth plate of CNP-transgenic mice (x50).

No typical histological change in the epiphyseal cartilage was found in CNP-transgenic mice at the prenatal stage, but as they grew, the height of the growth plate of long bones of the vetebrae of CNP-transgenic mice significantly increased at least at the age of 3 weeks or after (FIGS. 3A, B). Among the growth plate cartilage layers of the tibiae of 3-wk-old mice, both hypertrophic chondrocyte layer (234±12 $\mu$m versus 207±14 $\mu$m, n=4, p<0.05) and proliferative chondrocyte layer (215±3 $\mu$m versus 193±16 $\mu$m, n=4, p<0.05) of CNP-transgenic mice were longer than those of nontransgenic littermates. The hypertrophic chondrocyte layer and proliferative chondrocyte layer were shown to express type X collagen or type II collagen by in situ hybridization analysis (FIGS. 3E–H). Higher magnification revealed an increase of the size of chondrocytes (24.3±1.2 $\mu$m versus 21.2±1.3 $\mu$m, n=6, p<0.05) (FIGS. 3 C, D). The length of the resting chondrocyte layer was not changed even in CNP-transgenic mice. The band of BrdUrd positive chondrocytes was widened in CNP-transgenic mice relative to their nontransgenic littermates, though the number of BrdUrd positive chondrocytes was comparable (13.3±3% versus 12.5±2.9%, n=4) (FIGS. 3K, L). Von Kossa staining of the growth plate of the tibiae of 3-wk-old mice revealed that the epiphyseal trabecular bones formed by adjacent hypertrophic chondrocyte layer were obviously longer, and the volume of the trabecular bones was larger in CNP-transgenic mice than in their nontransgenic littermates (FIGS. 3I, J).

Example 6

Effects of the Cartilage-Specific Expression of CNP on Cultured Embryonic Tibiae from CNP-Transgenic Mice Tibiae from the fetus of CNP-transgenic mice or their nontransgenic littermates were dissected out on 16.5-d post coitus and cultured for 4 days in suspension in an artificial medium. To inhibit the effect of the endogenous CNP, the tibial culture was performed with a non-peptide NP receptor antagonist, HS-142-1 (Komatsu et al., Circ Res. 78:606–614, 1996) at a concentration of 50 mg/L in the medium. At the end of the culture period, the cultured tibiae were measured for their longitudinal length, and fixed and embedded for histological analysis. Sections of 5 $\mu$m in thickness were cut from the embedded specimen and stained with Alcian blue (pH 2.5) and counterstained with hematoxylin/eosin. The cGMP contents of the cultured tibiae were measured by RIA at the end of the 4-d culture period. Glycosaminoglycan synthesis of the cultured tibiae was assessed by measuring $^{35}SO_4$ incorporation (Mericq et al., Pediatr Res 47: 189–193, 2000). Namely, cultured tibiae of the CNP-transgenic mice and their nontransgenic littermates were labeled with 5 $\mu$Ci/ml Na$_2^{35}$SO$_4$ (Amersham, specific activity 100 mCi/mmol) for 1 h. The cultured tibiae were then rinsed three times for 10 min with Pack's saline (Sigma Chemical Co., St. Louis, Mo.), and then digested in 1.5 ml of fresh medium containing 0.3% papain for 24 h at 60° C. Then, the culture was incubated with 0.5 ml of 10% cetylpyridinium chloride (Sigma Chemical Co.)—0.2 M NaCl at room temperature for 18 h to precipitate glycosaminoglycan. The precipitate was washed three times with 1 ml of 0.1% cetylpyridinium chloride (Sigma Chemical Co.)—0.2 M NaCl and then dissolved in 1 ml of 23 N formic acid, after which the $^{35}SO_4$ content was determined by a liquid scintillation counter.

Figure 4:
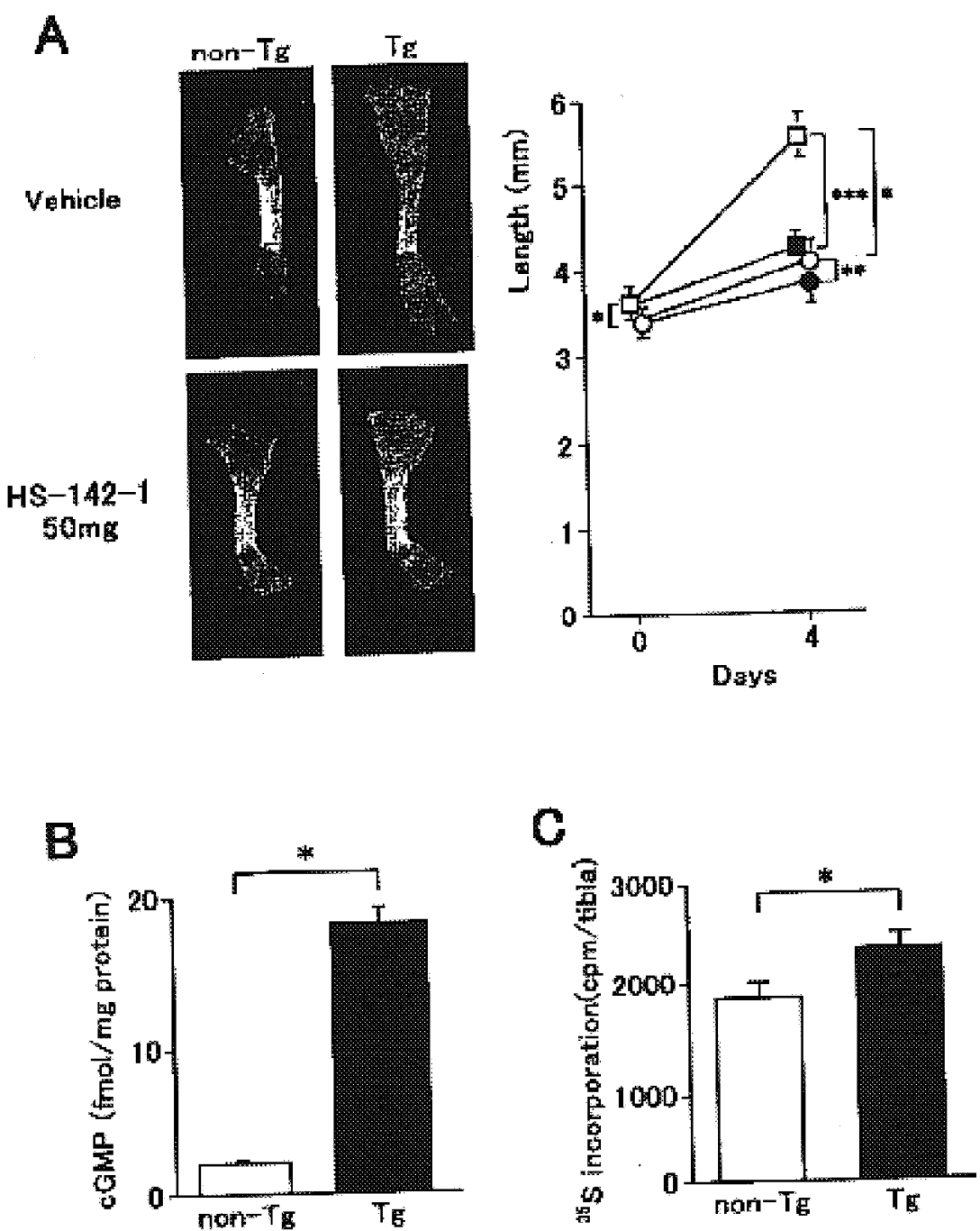
FIG. 4 shows organ culture of the tibiae of CNP-transgenic mice. A: The left panel shows photographs showing the appearance of the tibiae of 16.5-d fetal mice after 4-d culture from nontransgenic littermates (upper left), CNP-transgenic mice (upper right), nontransgenic littermates in the medium containing HS-142-1 (50 mg/L) (lower left) and CNP-transgenic mice in the medium containing HS-142-1 (50 mg/L) (lower right). The right panel shows a graph showing the time course of the growth of the length of the tibiae from the start to the end of 4-d culture. Open circles: nontransgenic littermates, n=6; open squares: CNP-transgenic mice, n=6; closed circles: nontransgenic littermates (HS-142-1), n=6; closed squares: CNP-transgenic mice (HS-142-1), n=6. *$P<0.05$ CNP-transgenic mice versus their nontransgenic littermates, $P<0.05$ HS-142-1-treated nontransgenic littermates versus untreated nontransgenic littermates, *$P<0.01$ HS-142-1-treated CNP-transgenic mice versus untreated CNP-transgenic mice. B: Graph showing the cGMP content of the cultured tibiae of the fetal CNP-transgenic mice (n=5). *$P<0.01$ CNP-transgenic mice versus their nontransgenic littermates. C: Graph showing $^{35}SO_4$ incorporation into the cultured tibiae of the fetal CNP-transgenic mice (n=6). *$P<0.05$ CNP-transgenic mice versus their nontransgenic littermates.
Figure 5:
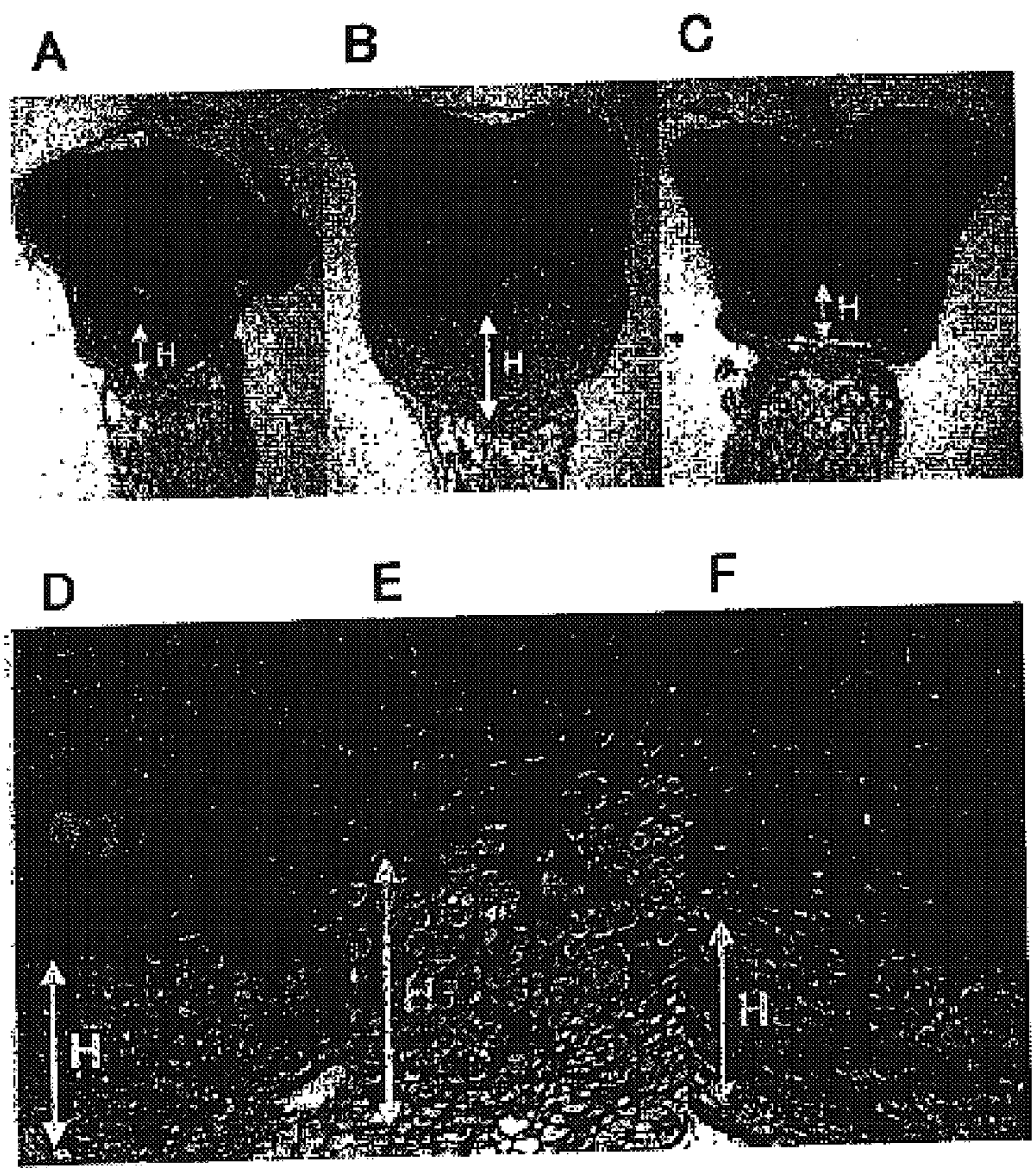
FIG. 5 shows photographs showing histochemical analysis of the cultured tibiae of CNP-transgenic mice (Alcian blue and hematoxylin/eosin staining). A: nontransgenic littermates (x25); B: CNP-transgenic mice (x25); C: CNP-transgenic mice (treated with HS-142-1) (x25); D: nontransgenic littermates (x200); E: CNP-transgenic mice (x200); F: CNP-transgenic mice (treated with HS-142-1) (x200).

Even before incubation, the tibial explants from CNP-transgenic mice were significantly longer than those from their nontransgenic littermates (FIG. 4A). During incubation, the tibial explants from CNP-transgenic mice increased prominently in longitudinal length and were about 35% longer than those from nontransgenic littermates at the end of the 4-d culture (n=6, FIG. 4A). The increase of the cartilagenous primordium was prominent (40% increase) among all parts of the tibial explant. HS-142-1 known to inhibit the effect of the endogenous CNP in cartilage could inhibit spontaneous growth of the tibial explants from nontransgenic littermates (FIG. 4A). Moreover, the increase in the length of the tibial explants from CNP-transgenic mice was completely abolished by HS-142-1 (50 mg/L) to the extent of the length of the tibiae from nontransgenic littermates treated with HS-142-1 (FIG. 4A). The content of cGMP in the cultured tibiae from CNP-transgenic mice was about 9 times higher than that in tibiae from nontransgenic littermates (18.7±1.2 fmol/mg protein versus 2.1±0.2 fmol/mg protein, n=5, FIG. 4B). Glycosaminoglycan synthesis was about 25% increased in tibiae from CNP-transgenic mice compared with those from their nontransgenic littermates (2300±170 cpm/tibia versus 1840±140 cpm/tibia, n=6, FIG. 4C). Histologically, the epiphyseal cartilage of the tibial explants from CNP-transgenic mice increased in the height of both proliferative chondrocyte layer (369±26 $\mu$m versus 287±14 $\mu$m, n=4, p<0.05) and hypertrophic chondrocyte layer (450±29 μm versus 294±16 μm, n=4, p<0.05), with the increased extracellular space stained by Alcian blue as cartilagenous matrix in the proliferative chondrocyte layer (FIGS. 5A, B). Also, the hypertrophic chondrocyte layer enlarged (17.8±0.8 μm versus 15.4±1.4 μm, n=6, p<0.05, FIG. 5D). Alteration induced by HS-142-1 at the same dose in the epiphyseal cartilage of the cultured tibiae from CNP-transgenic mice also disappeared.

Example 7

Analysis of CNP/FGFR3$^{ach}$-Double Transgenic Mice

Female CNP-transgenic mice and male FGFR3$^{ach}$-transgenic mice (obtained from Professor David M. Ornitz of Washington University, US) were mated. As FGFR3$^{ach}$-transgenic mice were originally produced on the FVB/N background, only F1 double transgenic mice were used in contrast to their CNP, FGFR3$^{ach}$ and nontransgenic littermates.

Figure 7:
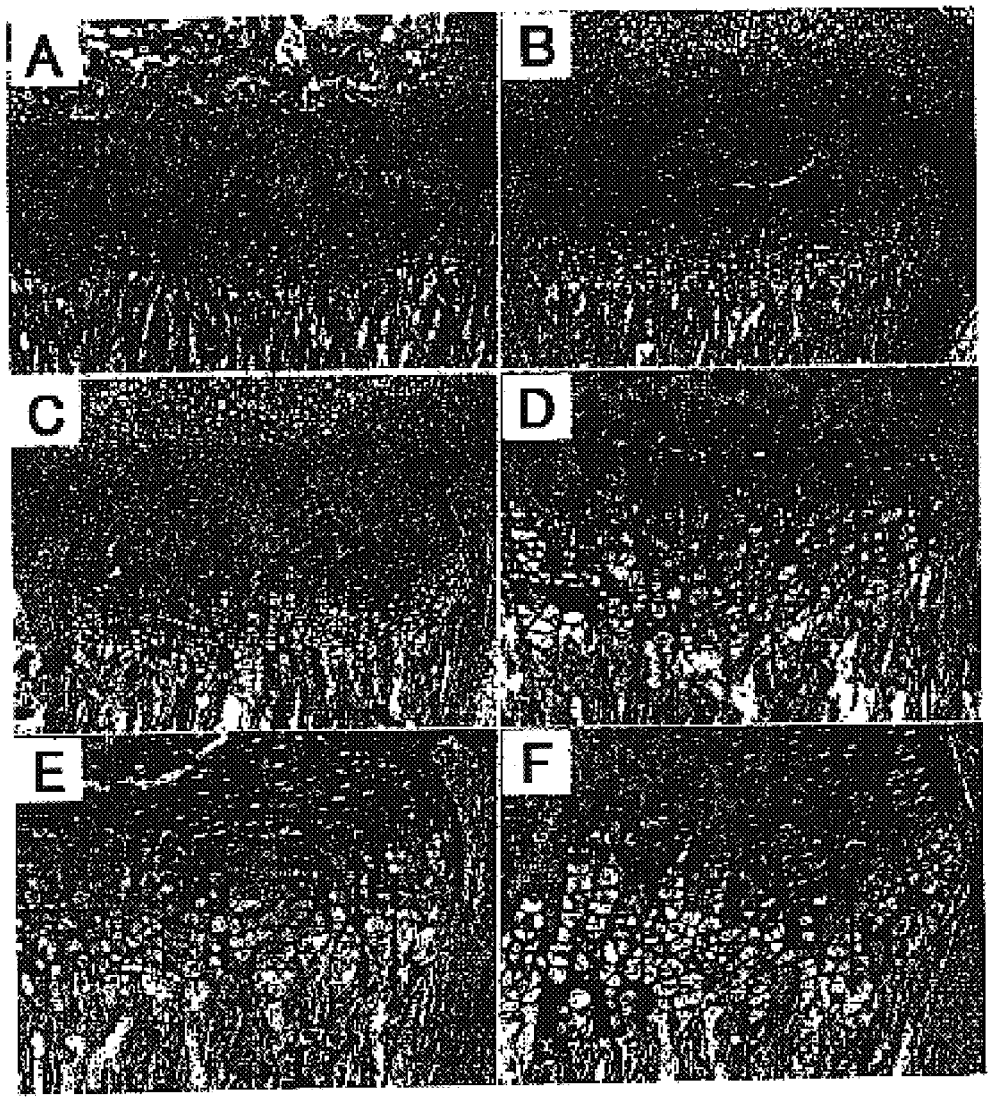
FIG. 7 shows photographs showing histochemical analysis of the tibial growth plate from 2-wk-old mice (Alcian blue and hematoxylin/eosin staining). A: nontransgenic littermates (x50); B: FGFR3$^{ach}$-transgenic mice (x50); C: CNP/FGFR3$^{ach}$-transgenic mice (x50); D: nontransgenic littermates (x100); E: FGFR3$^{ach}$-transgenic mice (x100); F: CNP/FGFR3$^{ach}$-transgenic mice (x100).

At the age of 3 months, CNP-transgenic mice were longer than their nontransgenic littermates and FGFR3$^{ach}$-transgenic mice were shorter than their nontransgenic littermates (FIG. 6A). The naso-anal length of CNP/FGFR3$^{ach}$-transgenic mice was almost comparable to that of the nontransgenic littermates. The CNP expression level in the cartilage of CNP/FGFR3$^{ach}$-transgenic mice was comparable to the expression level in CNP-transgenic mice (FIG. 6C). The growth curve of the naso-anal length of CNP/FGFR3$^{ach}$-transgenic mice, FGFR3$^{ach}$-transgenic mice and their nontransgenic littermates showed that the growth retardation in FGFR3$^{ach}$-transgenic mice was rescued by overexpression of CNP in the growth plate cartilage. At the age of 10 weeks, the naso-anal length of CNP/FGFR3$^{ach}$-transgenic mice was 94.7±4.0 mm, which was 8% longer than that of FGFR3$^{ach}$-transgenic mice (87.7±2.6 mm) and comparable to that of their nontransgenic littermates (97.0±4.2 mm) (FIG. 6B). Soft X-ray analysis revealed that the shortening of the length of the bones observed in FGFR3$^{ach}$-transgenic mice, including the naso-occipital length of the cranium and the longitudinal length of the humerus, femur and vertebrae (L1–7), was also partially rescued in CNP/FGFR3$^{ach}$-transgenic mice. The width of the cranium was not affected in either FGFR3$^{ach}$-transgenic or CNP/FGFR3$^{ach}$-transgenic mice (FIG. 6D). The microscopic analysis of the growth plate cartilage of the proximal tibiae from 2-wk-old CNP/FGFR3$^{ach}$-transgenic mice, FGFR3$^{ach}$-transgenic mice and their nontransgenic littermates showed that the height of the hypertrophic chondrocyte layer of FGFR3$^{ach}$-transgenic mice decreased as compared with that of nontransgenic littermates (169±15 μm versus 220±15 μm). It was recovered in CNP/FGFR3$^{ach}$-transgenic (229±21 μm, FIGS. 7A–C). However, the disordered alignment of the column of the hypertrophic chondrocytes and the enlarged extracellular matrix in the prehypertrophic and upper hypertrophic chondrocyte layers were observed in CNP/FGFR3$^{ach}$-transgenic mice in contrast to FGFR3$^{ach}$-transgenic mice and their nontransgenic littermates (FIGS. 7D–F). The size of each hypertrophic chondrocyte in CNP/FGFR3$^{ach}$-transgenic mice was significantly larger than that of FGFR3$^{ach}$-transgenic mice and their nontransgenic littermates (20.1±1.5 μm, 18.4±1.2 μm, 19.0±0.2 μm, n=6, p<0.05, FIGS. 7D–F). In the proximal tibiae of 10-wk-old mice, the secondary ossification center was not formed yet in FGFR3$^{ach}$-transgenic mice and CNP/FGFR3$^{ach}$-transgenic mice, whereas that was well organized in their nontransgenic littermates (FIGS. 7A–C).

Example 8

Study on the Interaction Between CNP and FGFR3 Using a Mouse Chondrocyte Strain

Cells of the mouse chondrocyte strain ATDC (J. Bone. Miner. Res., 12, 1174–1188, 1997; supplied from Assistant Professor Shukunami and Professor Hiraki of the Institute for Frontier Medical Sciences, Kyoto University) were pretreated with 1–10 ng/ml basic FGF (SIGMA), a ligand for FGFR3. Then, these cells were stimulated with $10^{-9}$–$10^{-7}$ M CNP and assayed for intracellular cGMP production by the RIA method (cyclic GMP Assay Kit available from YAMASA CORPORATION). Phosphorylation of p44 and p42 MAP kinases (ERK1/2) and expression of MAP kinase (MEK) and p44 MAP kinase (ERK1) after basic FGF stimulation were also assayed by Western blotting using phosphorylated MAP-K antibodies and MAP-K antibodies (both available from Cell Signaling Technology; MAP: mitogen-activated protein).

The results showed that intracellular cGMP production after CNP stimulation following pretreatment with 1 ng/ml basic FGF for 1 h decreased to 70% of control. Phosphorylation of ERK1/2 with basic FGF by pretreatment for 1 h was significantly inhibited by $10^{-7}$ CNP.

This revealed that CNP/GC-B systems and basic FGF/FGFR3 systems together influence intracellular transmission of information in chondrocytes.

ADVANTAGES OF THE INVENTION

Therapeutic agents for achondroplasia provided by the present invention can treat achondroplasia by acting as a gene for CNP, a CNP protein or a low molecular compound activating GC-B on a site other than directed by growth hormones. Therapeutic agents for achondroplasia of the present invention can offer an excellent therapy with improved QOL of patients by relieving burden and pain on the patients as compared with conventional orthopedic surgeries such as artificial hip joint replacement or leg lengthening. Moreover, transgenic animals disclosed herein can be used to test their efficacy against achondroplasia caused by mutations other than G380R in FGFR3.

What is claimed is:

1. A method for treating achondroplasia caused by the cartilage growth inhibition resulting from mutations in the gene for fibroblast growth factor receptor 3 (FGFR3), comprising administering a substance activating guanylyl cyclase B (GC-B).

2. The method of claim 1, comprising rescuing the cartilage growth inhibition by enlarging hypertrophic chondrocytes and increasing the extracellular matrix of the proliferative chondrocyte layer.

3. The method of claim 1 or 2, wherein the substance activating GC-B is a peptide.

4. The method of claim 3, wherein the peptide is a C-type natriuretic peptide (CNP).

5. The method of claim 4, wherein the CNP is CNP-22 or CNP-53.

* * * * *

(12) EX PARTE REEXAMINATION CERTIFICATE (7935th)
United States Patent
Nakao

(10) Number: US 6,743,425 C1
(45) Certificate Issued: Dec. 14, 2010

(54) THERAPEUTIC AGENTS FOR ACHONDROPLASIA

(76) Inventor: Kazuwa Nakao, 4-1-2, Ooekitakutsukake-cho, Nishikyo-ku, Kyoto-shi, Kyoto (JP)

Reexamination Request:
No. 90/009,412, Feb. 18, 2009

Reexamination Certificate for:
| | |
|---|---|
| Patent No.: | 6,743,425 |
| Issued: | Jun. 1, 2004 |
| Appl. No.: | 10/218,109 |
| Filed: | Aug. 14, 2002 |

(30) Foreign Application Priority Data

Sep. 28, 2001 (JP) .................................. 3015862001
Oct. 5, 2001 (JP) .................................. 310322/2001

(51) Int. Cl.
*A61K 38/22* (2006.01)

(52) U.S. Cl. .................. 424/94.61; 435/320.1; 435/325; 514/12; 536/23.1; 800/3; 800/9; 800/14; 800/18

(58) Field of Classification Search .................. None
See application file for complete search history.

(56) References Cited

U.S. PATENT DOCUMENTS 7,276,481 B2 10/2007 Golembo et al.

FOREIGN PATENT DOCUMENTS

| CA | 2 398 030 | 3/2003 |
|---|---|---|
| EP | 0769554 | 4/1997 |
| JP | 4252746 | 4/2009 |

OTHER PUBLICATIONS

Komatsu et al., Endocrinology, 129:1104–1106, 1991.*
Rosenzweig et al., "Atrial natriuretic factor and related peptide hormones," Annu. Rev. Biochem., 60:229–255, 1991.*
Sudoh et al., "A C–type natriuretic peptide (NP): new member of natriuretic peptide family identified porcine brain," Biochem. Biophys. Res. Commun., 168:863–870, 1990.*
Minamino et al., "N–terminally extended form of C–type natriuretic peptide (CNP–53) identified in porcine brain" Biochem. Biophys. Res. Commun., 170:973–979, 1990.*
U.S. Appl. No. 60/276,939, filed Mar. 20, 2001, Golembo et al.
Chusho et al., Dwarfism and early death in mice lacking C–type natriuretic peptide. *Proc. Natl. Acad. Sci. USA.* 98: 4016–21 (2001).
Mericq et al., Regulation of fetal rat bone growth by C–type Natriuretic peptide cGMP. *Pediatr. Res.* 47: 189–93 (2000).
Potter et al., Guanylyl cyclase–linked natriuretic peptide receptors: Structure and regulation. *J. Biol. Chem.* 276: 3057–60 (2001).
Segev et al., Restrained chondrocyte proliferation and maturation with abnormal growth place vascularization and ossification in human FGFR–3 $^{G380R}$ transgenic mice. *Hum. Molec. Genet.* 9: 249–58 (2000).
Wang et al., A mouse model of achondroplasia produced by targeting fibroblast growth factor receptor 3. *Proc. Natl. Acad. Sci. USA.* 96: 4455–60 (1999).
Abstract from Folia Endocrinologica Japonica (5$^{th}$ Annual Scientific Session of the Society of Cardiovascular Endocrinology and Metabolism) vol. 77; No. 2 (Sep. 20, 2001).
The Endocrine Society's 84$^{th}$ Annual Meeting (2002) Abstract OR54–1: Yasoda, et al. "Targeted Overexpression of C–Type Natriuretic Peptide in Chondrocytes Rescues Dwarfism in Achondroplasia."
Journal of Bone and Mineral Research (2002) vol. 17, Suppl. 1 (Sep. 2002) Abstract 1206: Yasoda, et al. C–type Natriuretic Peptide Elongates the Dwarfing Bones in Mice Model of Achondroplasia by Increasing the Extracellular Matrix of Growth Plate of Chondrocytes.
23$^{rd}$ Annual Meeting of the American Society for Bone and Mineral Research (Oct. 23, 2001) [Abstract—Yasoda, et al., "Targeted Overexpression of C–Type Natriuretic Peptide in the Growth Plate Rescued Dwarfism of the Transgenic Mice of Constitutive Active FGF Receptor 3."]
23$^{rd}$ Annual Meeting of the American Society for Bone and Mineral Research (Sep. 2001) [2001 Programs and Abstracts].
Folia Endocrinologica of Japonica vol. 77, No. 2 (Sep. 20, 2001) [Abstract of Meeting of Japanese Society for Endocrinology].
Horton (1996) *Progress in human chondyrodsplasias: molecular genetics.* Annals of the New York Academy of Sciences 785:150–9.
Naski, et al., (1998) "Repression of hedgehog signaling and BMP4 expression in growth plate cartilage by fibroblast growth factor receptor 3." Development 125:4977–4988.
Seino, et al. (2000) "Growth Hormone Theraphy in Achondroplasia." Horm Res 53(suppl 3): 53–56.
Vajo, et al. (2000) "The Molecular and Genetic Basis of Fibroblast Growth Factor Receptor 3 Disorders: The Achondroplasia Family of Skeletal Dysplasis, Muenke Carniosynostosis, and Crouzon Syndrome with Acanthosis Nigricans." Endocrine Reviews 21(1):23–39.
Webster and Donoghue (1996) "Constitutive activation of fibroblast growth factor receptor 3 by the transmembrane domain point mutation found in achondroplasia." The EMBO Journal 15(3): 520–527.
Yasoda, et al. (1998) "Natriuretic Peptide Regulation of Enchondral Ossification." The Journal of Biological Chemistry 273(19): 11695–11700.
Request for Ex parte Reexamination of U.S. Patent No. 6,743,425, filed Mar. 12, 2010 (Reexaminatin Control No. 90/010,911).

\* cited by examiner

*Primary Examiner*—Sharon Turner

(57) ABSTRACT

The present invention aims to provide novel therapeutic agents for achondroplasia caused by mutations in FGFR3.

Therapeutic agents for achondroplasia caused by the cartilage growth inhibition resulting from mutations in the gene for fibroblast growth factor receptor 3 (FGFR3), comprising a substance activating guanylyl cyclase B (GC-B) as an active ingredient are disclosed.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-5 is confirmed.

* * * * *